(12) United States Patent
McKay (10) Patent No.: US 11,517,696 B2
(45) Date of Patent: Dec. 6, 2022

(54) NOTCHED AIRWAY DEVICE AND USE THEREOF IN BAG-MASK VENTILATION AND ENDOTRACHEAL TUBE PLACEMENT

(71) Applicant: University of Saskatchewan, Saskatoon (CA)

(72) Inventor: William McKay, Saskatoon (CA)

(73) Assignee: University of Saskatchewan, Saskatoon (CA)

( * ) Notice: Subject to any disclaimer, the term of this patent is extended or adjusted under 35 U.S.C. 154(b) by 1059 days.

(21) Appl. No.: 16/098,530

(22) PCT Filed: Apr. 18, 2017

(86) PCT No.: PCT/CA2017/050473
§ 371 (c)(1),
(2) Date: Nov. 2, 2018

(87) PCT Pub. No.: WO2017/197498
PCT Pub. Date: Nov. 23, 2017

(65) Prior Publication Data
US 2021/0121653 A1 Apr. 29, 2021

Related U.S. Application Data

(60) Provisional application No. 62/333,915, filed on May 10, 2016.

(51) Int. Cl.
*A61M 16/04* (2006.01)
*A61M 16/00* (2006.01)
(Continued)

(52) U.S. Cl.
CPC .......... *A61M 16/0493* (2014.02); *A61B 1/01* (2013.01); *A61B 1/24* (2013.01); *A61B 1/2676* (2013.01);
(Continued)

(58) Field of Classification Search
CPC .. A61M 16/00; A61M 16/04; A61M 16/0402; A61M 16/0409; A61M 16/0488;
(Continued)

(56) References Cited

U.S. PATENT DOCUMENTS

| | | | | |
|---|---|---|---|---|
| 4,425,911 A | * | 1/1984 | Luomanen | A61M 16/0488 128/200.26 |
| 5,024,218 A | * | 6/1991 | Ovassapian | A61M 16/0495 128/207.14 |
| 5,174,284 A | * | 12/1992 | Jackson | A61M 16/0493 128/200.26 |

(Continued)

*Primary Examiner* — Colin W Stuart
(74) *Attorney, Agent, or Firm* — Kyle R Satterthwaite; Ryan W Dupuis; Ade & Company Inc (57) ABSTRACT

Novel airway devices and methods address complications of ventilating a patient with a mask; placing an endotracheal tube in an awake patient; and need for a bite block during flexible bronchoscopy and gastroscopy. The airway device features notches for engaging maxillary and mandibular teeth in a manner protracting the patient's mandible relative to the maxilla to open up the airway. This way, an open airway is easily maintained simply by holding the jaw closed against the device with the same hand used to operate a bag ventilator. A longitudinal channel in the device features a downwardly curved end wall for improved guidance of the endoscope into position. The channel is open sided at the top or bottom to allow rolling of the airway device off the endoscope into an offset position serving as a protective bite block and allowing feeding of the endotracheal tube along the endoscope.

16 Claims, 4 Drawing Sheets

(51) Int. Cl.
  *A61B 1/01* (2006.01)
  *A61B 1/24* (2006.01)
  *A61B 1/267* (2006.01)
  *A61B 1/273* (2006.01)

(52) U.S. Cl.
  CPC ....... *A61B 1/2736* (2013.01); *A61M 16/0084* (2014.02)

(58) Field of Classification Search
  CPC ............ A61M 16/049; A61M 16/0493; A61M 16/0495; A61M 16/0497; A61M 16/0048; A61M 16/0075; A61M 16/0078; A61M 16/0084; A61M 2210/0625; A61M 2210/0637; A61M 2210/065; A61C 7/08; A61B 1/01; A61B 1/24; A61B 1/2676; A61B 1/2736; A61B 1/2733
  See application file for complete search history.

(56) References Cited

U.S. PATENT DOCUMENTS

| | | | | |
|---|---|---|---|---|
| 5,590,643 | A * | 1/1997 | Flam | A61M 16/0488 128/207.14 |
| 6,792,947 | B1 * | 9/2004 | Bowden | A61M 16/0866 128/207.14 |
| 2001/0015206 | A1 * | 8/2001 | Arndt | A61M 16/0493 128/207.14 |
| 2010/0199998 | A1 * | 8/2010 | Matioc | A61M 16/0493 128/207.14 |
| 2011/0126840 | A1 * | 6/2011 | Ogilvie | A61M 16/0488 128/207.14 |
| 2012/0283513 | A1 * | 11/2012 | Leeflang | A61B 1/00154 600/114 |
| 2015/0238722 | A1 * | 8/2015 | Al-Ali | A61M 16/085 128/205.13 |
| 2019/0070374 | A1 * | 3/2019 | Fogarty | A61M 16/024 |

* cited by examiner

NOTCHED AIRWAY DEVICE AND USE THEREOF IN BAG-MASK VENTILATION AND ENDOTRACHEAL TUBE PLACEMENT

FIELD

The present application relates generally to airway devices and more specifically to airway devices with notched areas in their topside and underside for engagement with a patient's anterior teeth to hold the patient's mandible in a forward thrusted position that encourages an unobstructed airway; and to designs and uses for such airway devices, which are particularly useful during bag-mask ventilation, endotracheal tube placement, and endoscopy.

BACKGROUND

The present application relates primarily to three healthcare areas: namely obtaining and maintaining an unobstructed airway during ventilation of an unconscious patient with a bag-mask resuscitator, placing an endotracheal tube in a conscious patient, and performing lung or upper gastrointestinal endoscopy. The application also relates to the issue of gagging when these procedures are performed on conscious patients.

Forces and movements described herein make use of anatomical terms typically associated with an erect posture; thus, although most patients requiring the described treatments are supine, "upward" will mean away from the feet and toward the top of the head (i.e. superiorly of the patient) rather than toward the ceiling, and forward will mean forward relative to the face (i.e. anteriorly of the patient).

A conscious person automatically keeps an unobstructed airway without conscious effort by adjusting the tone of the small muscles of the pharynx (the airway from mouth to larynx) and the larynx (the structure that acts as the portal to the trachea). This tone is lost in comatose or anesthetized patients. Then the airway may be obstructed by the tongue and other soft tissues, making bag-mask ventilation difficult or impossible. This obstruction can sometimes be overcome by introducing an oral airway into the mouth and/or by jaw thrust; pushing the jaw forward relative to the face. However, bag-mask ventilation even with these measures often provides inadequate ventilation except in the hands of very experienced practitioners such as anesthesiologists. This is because of the complex hand maneuver required to pull the jaw forward to open the airway (the jaw thrust) while simultaneously pushing the mask firmly backwards (i.e. posteriorly) onto the face to achieve a good seal. This skilled maneuver takes considerable time to teach, learn, and maintain. Many health care workers (nurses, family practitioners, and others) are called upon infrequently to resuscitate patients who are not breathing, meaning that they are not skillful at maintaining proper jaw thrust during bag-mask ventilation due to infrequent use and practice of this skill.

The temporomandibular jaw joint is a complex joint. It has a hinge function providing pivotal motion when the jaw opens, closes, and bites hard. It is simple for a practitioner to learn to close the jaw firmly through hinged motion by pressing the mandible toward the maxilla. As well as being a simple hinge, the jaw can subluxate (partially dislocate) to enable the mandible to angulate from side to side relative to the maxilla and thus perform the complex chewing maneuvers necessary for an omnivore. By subluxing both temporomandibular joints at once, one can also advance the mandible forward relative to the maxilla and rest of the face (jaw thrust). Most people can bite their upper lip with their lower teeth—effectively a jaw thrust. This tends to reduce soft tissue obstruction and opens the airway to allow good ventilation.

In a supine patient, gravity acts to allow the tongue, and other soft tissues from the front of the airway to fall back and lie against the back of the airway, causing obstruction. Jaw thrusting usually overcomes these obstructions. An experienced practitioner typically holds the jaw forward with the fifth finger behind the mandible to apply jaw thrust while pressing firmly backwardly on the mask with his/her thumb and index finger and while also pressing upwardly on the mandible with the middle and ring fingers. This procedure is more difficult than it looks. By comparison, an inexperienced practitioner will typically place all fingers below the mandible, where he/she can apply only hinge pressure. Hinge pressure is easy to apply for the novice or for the practitioner who is rarely called upon to mask ventilate (most physicians and nurses), but cannot be relied upon to provide good ventilation for most unconscious patients, especially those who are edentulous or obese. In these scenarios, a Guedel-type airway will often be used to hold the tongue forward and allow ventilation, but even such devices cannot be relied on exclusively to do so without jaw thrust.

In summary, it is relatively easy to hold a mask on firmly while pulling the jaw into a closed position by applying hinge force, but it can be difficult to provide effective jaw thrust while performing bag-mask ventilation.

Making it easier to thrust the jaw forward and hold it there while bag-mask ventilating could be helpful for the occasional or unskilled user. Beginners (and occasional users) typically just push the mask downward on the face, thereby increasing the obstruction to ventilation. Experts grasp the mandible, open the mouth (through pivotal hinge action), thrust the jaw to protract the mandible, and then apply the mask without releasing the jaw thrust. More specifically, the expert typically places their fifth finger behind the angle of the jaw to pull forward; with their fourth finger pulling forward on the soft tissues, their middle finger pushing the mandible upwardly, and their thumb and index fingers pushing the mask backward into firm compliance with the face. All of these finger positions are subtly adjusted for different bite and soft tissue configurations, and so the procedure requires significant skill and dexterity.

It may be desirable to provide a solution enabling confident un-obstruction of the airway during use of a bag-mask resuscitator by trainees and non-specialized practitioners of lesser skill and/or experience level than anesthesiologists or other experienced/specialized practitioners who have worked to develop the forgoing technique.

Regarding elective diagnostic flexible bronchoscopy and gastroscopy, a bite block may be used to protect the very delicate scopes from damage from inadvertent biting by the patient. Such procedures are performed thousands of times per day in Canada and the USA, and typically use such bite blocks to protect the scope, but conventional bite blocks do not optimally position the jaw for scoping.

Turning to placement of an endotracheal tube in a conscious patient, it is desirable to provide an oral airway that: (a) protects the bronchoscope from damage by biting while also opening the airway, (b) causes minimal stimulation of gag, choke, or cough reflexes, and (c) directs the bronchoscope toward the trachea.

Commonly, the trachea is intubated by looking down into the mouth and throat of an anesthetized or comatose patient with a lighted device called a direct laryngoscope. A variety of congenital and acquired deformities of the face, mouth, or throat can make intubation of the trachea with this method difficult or impossible. For airway situations where intubation is known or suspected to be difficult, a technique is used that employs topical anesthesia of the mouth and throat followed by entering the trachea with a flexible bronchoscope while the patient is awake ("awake fibre-optic intubation"). The bronchoscope is armed with an endotracheal tube to slide over it into the trachea when the bronchoscope is in the trachea. Meanwhile, the awake patient can assure his own ventilation by breathing around the bronchoscope. Biting on the bronchoscope can cause breakage of the glass fibers inside making it impossible to see the trachea and requiring expensive repairs.

Special airway devices have been developed to direct the bronchoscope toward the trachea and prevent it from being bitten by the patient, including the Williams Airway Intubator (Williams Airway Intubator Ltd, Calgary, Canada), the Ovassapian Fiber Optic Airway (Medline Industries, Inc. One Medline Place Mundelein, Ill. 60060), and the Berman Intubating Airway (Vital Signs, Totowa, N.J., USA). It is easily appreciated that all of these are essentially modified Guedel airways.

An important problem is commonly encountered in attempting awake fibre-optic intubation. Humans are very sensitive to hard foreign bodies touching the tissues of the pharynx (back of the mouth—gagging and retching); within the larynx (voice box—spasm and choking); and within the trachea (violent coughing). Topical local anesthetic or nerve blocks are commonly used to anesthetize the airway to enable awake intubation. The most sensitive and most difficult reflex to adequately anesthetize and supress in many patients is the gag reflex, which is activated by pressure on the back wall of the airway behind the tongue. All of the aforementioned airway devices, except the simple bite block, can cause gagging when inserted.

Other airway devices and bite blocks useful in placement of an endotracheal tube with a bronchoscope include those shown in U.S. Pat. Nos. 4,425,911, 5,590,643 and 8,146,601 and U.S. Patent Application Publication Number 2012/199140.

Of these references, U.S. Pat. No. 5,590,643 discloses an airway device with top and bottom notches therein respectively engageable by anterior maxillary and mandibular teeth and positioned relative to one another so that placement of the mandibular teeth in one of the bottom notches achieves a thrusted or protracted position of the mandible, which encourages opening of the patient's airway into an unobstructed state. The airway described in U.S. Pat. No. 5,590,643 includes a central longitudinal bore through which an endoscope can be passed, followed by an endotracheal tube fed along the endoscope. A potential drawback of this design is that while the through-bore enables such feeding of the bronchoscope and endotracheal tube through it, the larger endotracheal tube connector at the proximal end of the endotracheal tube cannot fit through this central bore of the airway, and so once the endotracheal tube has been successfully placed, removal of the airway requires that the endotracheal tube connector be removed from the endotracheal tube to allow the airway to be slid off of the endotracheal tube. Endotracheal tube connectors are normally fitted on the endotracheal tube by a tapered force-fit, and there is potential danger that pulling the connector in an attempt to remove it from the endotracheal tube will withdraw the endotracheal tube from the patient's trachea.

In view of the forgoing, there is room for improvement in the design and use of airway devices.

SUMMARY

An embodiment of the disclosure is an airway device comprising:
a body comprising:
a topside and an opposing underside separated in a height direction of said body;
a proximal end and opposing distal end separated in a longitudinal direction of said body;
an upper notch defined in the topside of the body and extending in a lateral direction transverse to the longitudinal and height directions for receipt of anterior maxillary teeth of a patient in said upper notch;
a lower notch defined in the underside of the body and extending in the lateral direction for receipt of anterior mandibular teeth of the patient in said lower notch, said lower notch being positioned relative to the upper notch in the longitudinal direction of the airway so as to position the patient's mandible in a protracted position to encourage an unobstructed state of the patient's airway; and
a longitudinal channel recessed into the underside of the body and spanning longitudinally from the proximal end of the body toward the opposing distal end thereof, the longitudinal channel having a cross-sectional area of sufficient size to accommodate an outer diameter of an endoscope therein to enable introduction of said endoscope orally into the patient while the body is held in a working position engaged between the maxillary and mandibular teeth of the patient at the upper and lower notches of the body.

The endoscope may be a bronchoscope or a gastroscope.

Another embodiment of the disclosure is an airway device comprising:
a body comprising:
a topside and an opposing underside separated in a height direction of said body;
a proximal end and opposing distal end separated in a longitudinal direction of said body;
an upper notch defined in the topside of the body and extending in a lateral direction transverse to the longitudinal and height directions for receipt of anterior maxillary teeth of a patient in said upper notch;
a lower notch defined in the underside of the body and extending in the lateral direction for receipt of anterior mandibular teeth of the patient in said lower notch, said lower notch being positioned relative to the upper notch in a longitudinal direction of the airway so as to position the patient's mandible in a protracted position to encourage an unobstructed open state of the patient's airway; and
a longitudinal channel recessed into either the underside or the topside of the body and spanning longitudinally from the proximal end of the body toward the opposing distal end thereof, the longitudinal channel having a cross-sectional area of sufficient size to accommodate an outer diameter of an endoscope therein to enable introduction of said endoscope orally into the patient while the body is held in a working position engaged between the maxillary and mandibular teeth of the patient at said upper and lower notches of the body;
wherein the longitudinal channel terminates in a curved downturned wall imparting directional guidance of the endoscope downwardly from the longitudinal channel.

Yet another embodiment of the disclosure is an airway device and a bag-mask resuscitator in combination, said airway device comprising a transversely oriented upper notch defined in a topside of the airway for receipt of anterior maxillary teeth of the patient within said upper notch in a working position of the airway device, and at least one transversely oriented lower notch defined in an underside of the airway for receipt of anterior mandibular teeth of the patient within said lower notch in the working position of the airway device, said lower notch being positioned relative to the upper notch in a longitudinal direction of the airway so as to position the patient's mandible in a protracted position to encourage an unobstructed state of the patient's airway in the working position of the airway device, the airway device being arranged such that single-handed urging of the patient's mandible in a hinged manner toward the patient's maxilla by a same hand that is simultaneously used to urge a mask of the bag-mask resuscitator against a facial area of the patient maintains the working position of the airway device between the maxillary and mandibular teeth of the patient so as to thereby maintain the protracted position of the patient's mandible.

A further embodiment of the disclosure is a method of preparing a patient for ventilation by a bag-mask resuscitator, the method comprising:

providing an airway device comprising a transversely oriented upper notch defined in a topside of the airway for receipt of anterior maxillary teeth of the patient within said upper notch, and a transversely oriented lower notch defined in an underside of the airway for receipt of anterior mandibular teeth of the patient within said lower notch, said lower notch being positioned relative to the upper notch in a longitudinal direction of the airway so as to position the patient's mandible in a protracted position to encourage an unobstructed state of the patient's airway;

placing the airway device in a working position in which maxillary teeth of the patient engage said upper notch in the topside of the airway device and mandibular teeth of the patient engage in said lower notch in the underside of the airway device, thereby achieving the protracted position of the patient's mandible and encouraging the unobstructed state in the patient's airway;

simultaneously and one handedly urging hinged closure of the mandible toward the maxilla to maintain the working position of the airway between maxillary and mandibular teeth while urging a mask of the bag-mask resuscitator against a facial area of the patient.

Another embodiment of the disclosure is the use of a bag-mask resuscitator and an airway device in combination, said airway device comprising a transversely oriented upper notch defined in a topside of the airway for receipt of anterior maxillary teeth of the patient within said upper notch in a working position of the airway device, and at least one transversely oriented lower notch defined in an underside of the airway for receipt of anterior mandibular teeth of the patient within said lower notch in the working position of the airway device, said lower notch being positioned relative to the upper notch in a longitudinal direction of the airway so as to position the patient's mandible in a protracted position to encourage an unobstructed state of the patient's airway in the working position of the airway device, the airway device being arranged such that single-handed urging of the patient's mandible in a hinged manner toward the patient's maxilla by a same hand that is simultaneously used to urge a mask of the bag-mask resuscitator against a facial area of the patient maintains the working position of the airway device between the maxillary and mandibular teeth of the patient so as to thereby maintain the protracted position of the patient's mandible.

Another embodiment of the disclosure is a method comprising:

providing an airway device having a topside and an opposing underside separated in a height direction of said body, a proximal end and opposing distal end separated in a longitudinal direction of said body, an upper notch defined in the topside of the body and extending in a lateral direction transverse to the longitudinal and height directions for receipt of anterior maxillary teeth of a patient in said upper notch, a lower notch defined in the underside of the body and extending in the lateral direction for receipt of anterior mandibular teeth of the patient in said lower notch, and a longitudinal channel recessed into either the underside or the topside of the body and spanning longitudinally from the proximal end of the body toward the opposing distal end thereof;

with the airway device received between the anterior maxillary and mandibular teeth of the patient with the mandible of the patient in a protracted position maintained by engagement of the anterior maxillary and mandibular teeth in the upper and lower notches respectively, passing a distal end of an endoscope through the longitudinal channel to a target destination in the patient; and while maintaining the distal end of the endoscope at the target destination, withdrawing the longitudinal channel of the airway device from an embraced position about the endoscope by freeing the endoscope from the longitudinal channel through an open top or bottom thereof at the topside or underside of the airway device.

In one embodiment, the endoscope is a bronchoscope, the target destination is the patient's trachea, and freeing of the bronchoscope from the airway device enables feeding of an endotracheal tube along said bronchoscope into the patient's trachea independently of the airway device.

Yet another embodiment of the disclosure is a method of using an airway device and an endoscope in combination, said method comprising with the airway device in a previously achieved position received between the anterior maxillary and mandibular teeth of the patient that are respectively engaged in upper and lower notches at a topside and underside of said airway device with the mandible of the patient in a protracted position maintained by engagement said anterior maxillary and mandibular teeth in said upper and lower notches, and with an endoscope in another previously achieved position reaching through the longitudinal channel to a target destination in the patient, withdrawing the longitudinal channel of the airway device from an embraced position about the endoscope by freeing the endoscope from the longitudinal channel through an open top or bottom thereof at the topside or underside of the airway device.

Another embodiment of the disclosure is the use of an airway device and endoscope in combination, wherein:

said airway device comprises a topside and an opposing underside separated in a height direction of said airway device, a proximal end and opposing distal end separated in a longitudinal direction of said airway device, an upper notch defined in the topside of the airway device and extending in a lateral direction transverse to the longitudinal and height directions for receipt of anterior maxillary teeth of a patient in said upper notch, a lower notch defined in the underside of the body and extending in the lateral direction for receipt of anterior mandibular teeth of the patient in said lower notch, and a longitudinal channel recessed into either the underside or the topside of the airway device and spanning longitudinally from the proximal end of the airway device toward the opposing distal end thereof;

said longitudinal channel being arranged to:

accommodate passage of a distal end of the endoscope through the longitudinal channel to a target destination in the patient with the airway device received between the anterior maxillary and mandibular teeth the patient with the mandible of the patient in a protracted position maintained by engagement of the anterior maxillary and mandibular teeth in the upper and lower notches respectively; and enable withdrawal of the longitudinal channel of the airway device from an embraced position about the endoscope by separation of the endoscope from said longitudinal channel via an open top or bottom thereof at the topside or underside of the airway device so as to free the endoscope from the airway device.

In an embodiment, withdrawing the longitudinal channel of the airway device from the embraced position comprises using a rolling motion of the airway device about a longitudinal axis to withdraw the longitudinal channel from about the endoscope.

In another embodiment, withdrawing the longitudinal channel of the airway device from the embraced position comprises moving the airway device into a lateral position received between posterior maxillary and mandibular teeth on one side of the patient's dental arch, where the device serves as a bite block to protect the endoscope from biting.

BRIEF DESCRIPTION OF THE DRAWINGS

An exemplary embodiment of the present application will now be described in greater detail with reference to the drawings in which.

In the drawings like characters of reference indicate corresponding parts in the different figures.

It is intended that the embodiments and figures disclosed herein are to be considered illustrative rather than restrictive.

DETAILED DESCRIPTION

FIG. 1 illustrates an airway device 10 according to one embodiment of the present disclosure. The airway device 10 of the illustrated embodiment is defined in its entirety by a unitary body 12 of molded plastic such as polyurethane, and for example having a hardness value between Shore 40a to 50a. The body has a proximal end 14 and a distal end 16 lying opposite to one another in a longitudinal direction of the body, and a topside 18 and underside 20 that lie opposite to one another in a height direction that is orthogonal to the longitudinal direction. A transverse width direction of the body lies orthogonal to the longitudinal and height directions, and separates opposing lateral sides 22, 24 of the body from one another. In the illustrated embodiment, the body 12 has a uniform width throughout.

Figure 1A:
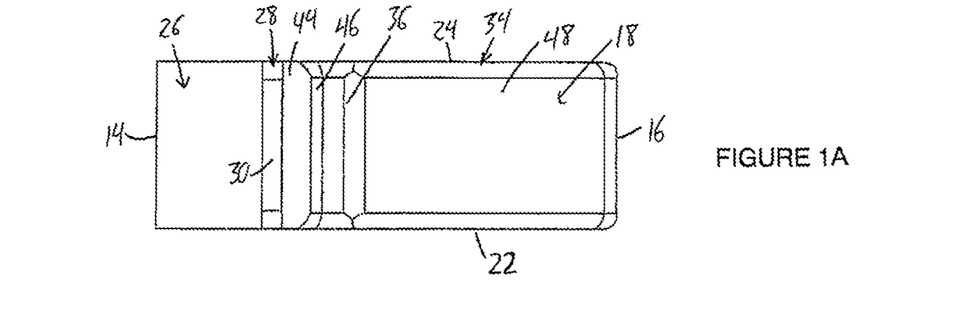
FIGS. 1A, 1B, 1C, 1D and 1E are overhead plan, side elevational, proximal end elevational, distal end elevational, and cross-sectional views of an airway device of the present application, the cross-section of FIG. 1E being taken along line E-E of FIG. 1A.
Figure 1B:
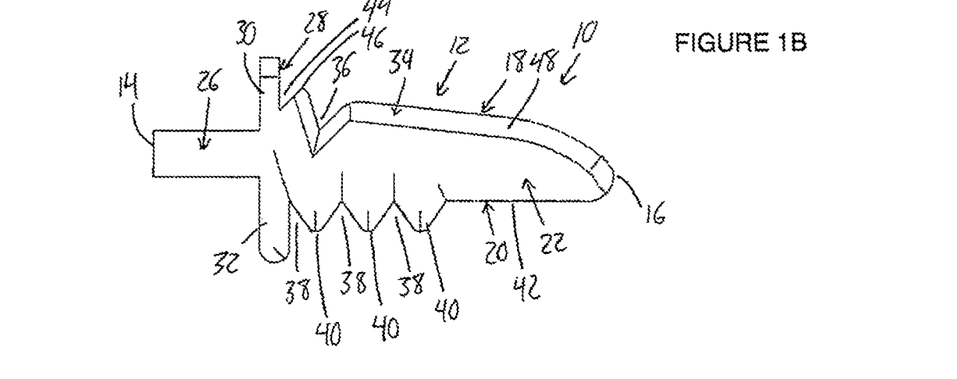
Figure 1C:
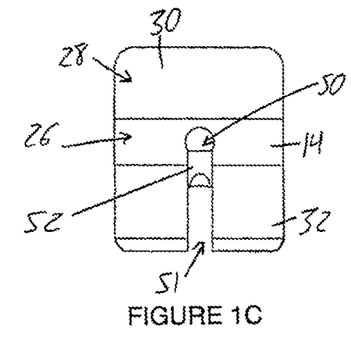

In the longitudinal direction, the airway device has three distinct sections, though these sections are seamlessly integral with one another in the molded unitary body structure of the illustrated embodiment. Starting from the proximal end 14, the first section is a tab-like grip 26 that is flat at both the topside and underside of the body, and has a uniform thickness or height that is measured between the topside and underside.

Next, a flanged section 28 features a top flange 30 standing perpendicularly upward from the flat topside of the grip 26, and a bottom flange 32 depending perpendicularly downward from the flat underside of the grip 26. Each flange 30, 32 spans the full width of the body. The flanged section 28 is of greater height than the other two sections, with the top flange reaching further upward than any other point at the topside of the body, and the bottom flange likewise reaching further downwardly than any other point at the underside of the body.

Finally, a bite section 34 spans from the flanged section to the distal end 16 of the body. At the bite section 34, the topside of the body features a single upper notch 36 recessed therein to span fully between the lateral sides of the body in the width direction near the top flange 30 of the flanged section, while the underside of the body features a set of multiple lower notches 38 recessed therein to span fully between the lateral sides of the body in the width direction near the bottom flange 32 of the flanged section.

The illustrated embodiment features three of these lower notches 38, one of which immediately neighbours the bottom flange 32. Alternating with the notches in the longitudinal direction of the body are three protuberances 40 which project downwardly from reference plane occupied by a flat area 42 of the bite section's underside. This flat area 42 reaches longitudinally from the third protuberance to the distal end 16 of the body. In the illustrated embodiment, the single upper notch 36 in the topside of the body generally aligns with the first protuberance 40 at the underside of the body 12. By separating the lower notches with protuberances and aligning the upper notch with one of the protuberances, as opposed to simply recessing the lower notches in an otherwise flat area of the body's underside, a notable thickness of the body is maintained beneath the upper notch 36 so as not to sacrifice the structural integrity of the device under bite-pressure applied by the patient during use of the airway device 10.

At the topside of the bite section 34, the top flange 30 of the flanged section 28 is immediately neighboured by a small valley 44 of lesser depth than the upper notch 36, followed by a small peak 46 that separates the valley 44 and upper notch 36 from one another. At the opposite side of the upper notch 36, the topside of the bite section 34 has a sloped area 48 that continues longitudinally toward the distal end 16 of the body with a gradual slope that declines downwardly toward the reference plane occupied by the flat area 42 at the underside of the bite section 34. As a result, the bite section is tapered in height as one moves longitudinally from the upper notch 36 to the distal end 16.

Figure 1D:
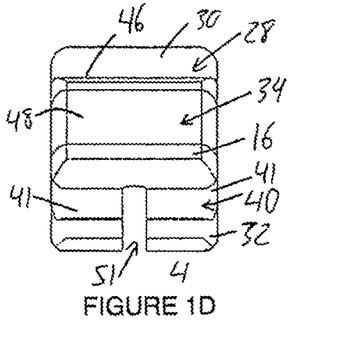
Figure 1E:
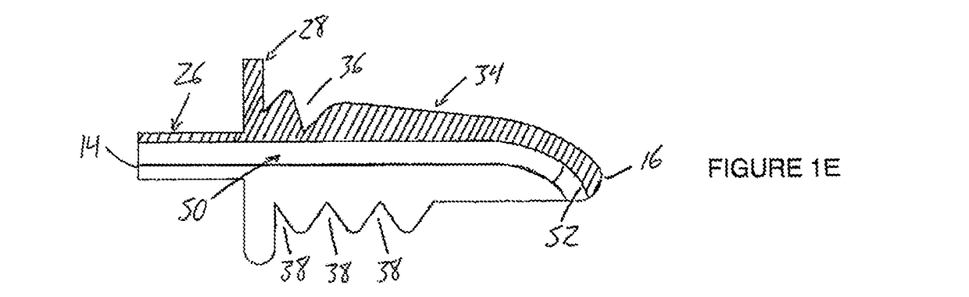

The airway device 10 also features a longitudinal channel 50 recessed into the underside of all three sections and spanning a substantial majority of the body's length from the proximal end 14 of the body 12 to a position near, but stopping short of, the distal end 16 of the body 12. The channel opens longitudinally through the proximal end 14 of the body, thereby defining an inlet opening of the channel at the proximal end 14. The opposing outlet end of the channel is longitudinally closed, specifically being terminated by a concavely downturned wall 52 that curves downwardly from the roof of the channel. The width of the longitudinal channel exceeds the outer diameter of a bronchoscope with which the airway may be used to prepare a patient for receipt of a cooperating endotracheal tube, as described in more detail herein below. Accordingly, the cross-sectional area of the channel 50 accommodates the bronchoscope therein via insertion of the bronchoscope's distal end through the inlet opening of the channel at the proximal end 14 of the airway device 10. With reference to FIG. 1D, it can be seen how each of the underside protuberances 40 are bisected by an open bottom 51 longitudinal channel 50, and thus split into to halves 41 each residing on a respective side of the channel. From this, it will be understood that the lower notches 38 situated between the underside protuberances 40 are likewise bisected by the open bottom 51 of the longitudinal channel 50, whereby each lower notch is a split-notch composed of two half notches residing on opposing sides of the longitudinal channel 50.

Figure 2:
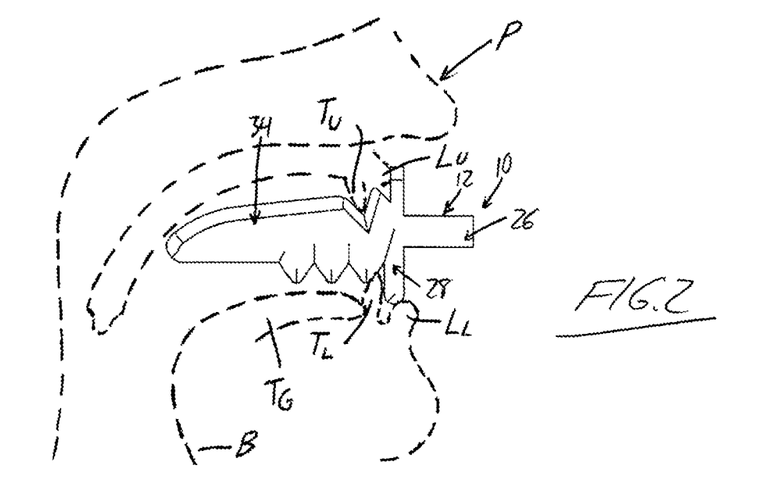
FIG. 2 is a schematic illustration of the airway device of FIG. 1 in a working position engaged between anterior teeth of a patient so as to maintain the mandible in a protracted position establishing an unobstructed state of the patient's airway.
Figure 3:
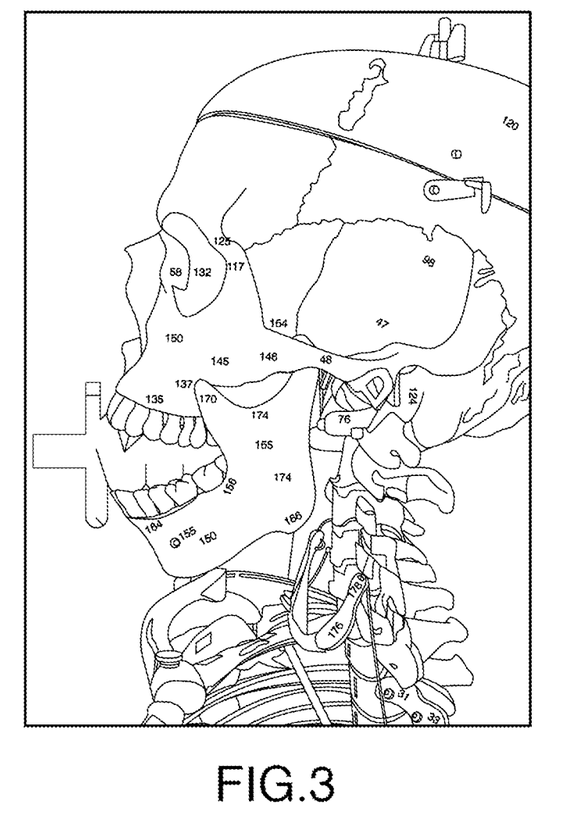
FIG. 3 shows the working position of FIG. 2 on a skeletal model.

With reference to FIG. 2, the airway device is used by inserting the bite section 34 into a patient's open mouth. The flanged section 28 serves as a stop intended to limit this insertion of the airway device by eventual contact with the patient's upper and lower lips $L_U$, $L_L$. With anterior maxillary teeth, or upper teeth, $T_U$ of the patient P engaged into the upper notch 36, the patient's mandible is thrusted as forwardly far as possible into a protracted position relative to the maxilla, and, by hinged closure of the thrusted mandible toward the maxilla, the patient's anterior mandibular teeth, or lower teeth $T_L$, are engaged into one of the lower notches 38 reached by this fully thrusted position of the jaw. The airway device is thus held in this working position between the anterior maxillary and mandibular teeth, and this held working position of the airway device maintains the thrusted state of the jaw, which as described above serves to open up the patient's airway. As shown, the airway device is free of any tongue retraction means depending downwardly from the remainder of the body at the distal end thereof to retract the base B of the tongue $T_G$ forwardly, thereby terminating well short of the throat to avoid gagging or other discomfort, and instead relies solely on the thrusted position of the jaw to open the airway.

Figure 4:
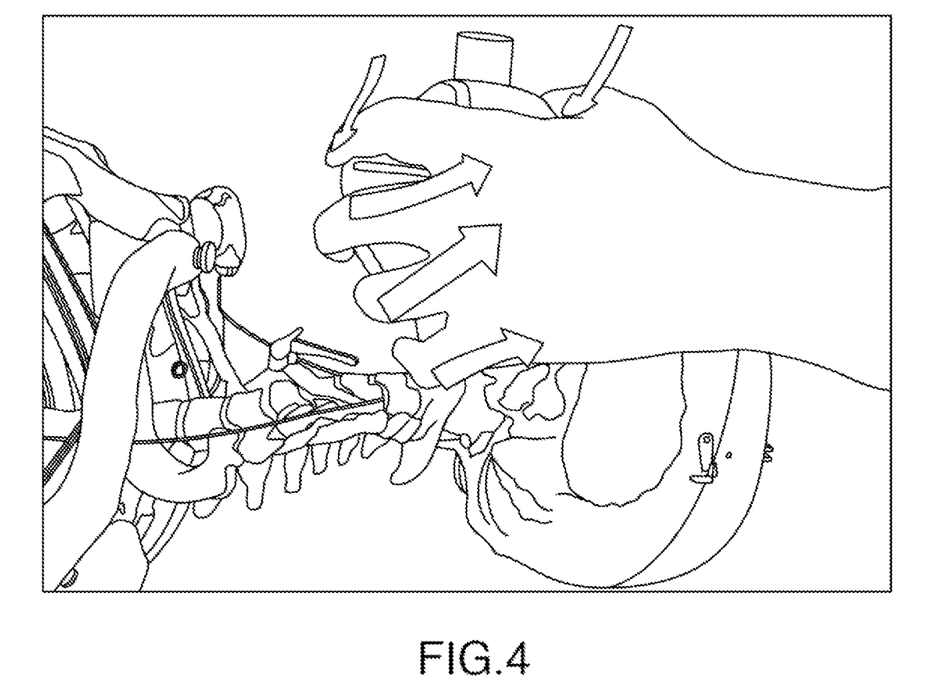
FIG. 4 illustrates the ability of an unskilled practitioner to one-handedly apply hinge pressure to the jaw, thereby holding the airway device in the working position to maintain the protracted mandible position, while holding a mask of a bag-mask resuscitator in sealed condition against the patient's face.

In a first mode of use, the airway device 10 is used in accompaniment to a bag-mask resuscitator on an unconscious patient. In such instance, the opening of the jaw to accommodate insertion of the of the airway device, if the patient's mouth is not already sufficiently open, and the subsequent thrusting and hinged closure of the jaw to engage the airway device 10 in the working position between the patient's anterior teeth, is performed by the practitioner responsible for administering ventilation with the bag-mask resuscitator. During this placement of the airway device 10, the practitioner can use both hands to perform the jaw thrusting action. With the airway device 10 in place, the airway is thus opened by the thrusted state of the jaw, and the practitioner can then use one hand to apply hinge pressure to maintain the closed state of the jaw against the airway. Now the practitioner can lower the mask of the bag-mask resuscitator into place against the wearer's face with the other hand, whereupon the thumb and index finger of the jaw-holding hand can then be situated over the rim of the mask to hold in it in sealed condition with the patient's facial areas around the nose and mouth. This is shown in FIG. 4, where the middle, fourth and fifth fingers of the practitioner's first hand continue to apply upward (superior) pressure to the underside of the mandible to maintain the closed and thrusted state thereof against the airway device, while the thumb and index finger of the same hand hold the mask in place, thereby freeing the practitioner's second hand to operate the bag of the resuscitator in a conventional manner to administer air to the patient through the mask. The one-handed maintenance of the jaw requires only exertion of hinge pressure on the jaw because the thrusted state of the jaw is maintained by the airway device, and so the dexterity required to hold the jaw and mask in place is reduced. Accordingly, use of an airway device of the disclosure may reduce the skill and expertise required to maintain an open airway.

In a second mode of use, the airway device 10 is used to prepare a patient for awake intubation. To use the airway device 10 for awake intubation, after anesthetizing the airway in the usual fashion, the biting section 34 of the airway device 10 is inserted into the mouth by the practitioner or patient, who then ensures that the anterior maxillary teeth (upper incisors) $T_U$ are settled in the upper notch 36. At this point, the patient's mandible is thrust forward and then closed upwardly so that the anterior mandibular teeth $T_L$ bite into in the farthest-forward notch that is comfortably reached by the patient's thrusted mandible. During awake intubation procedures, the practitioner can simply request that patients perform these jaw thrust and closure steps themselves. Many patients requiring awake intubation have a difficult airway because the jaw is small, and the bottom incisors are farther than usual behind the uppers, hence the inclusion of several lower-incisor notches 38 in the illustrated embodiment. It will be appreciated however that the number of lower notches 38 may be increased or decreased from the three shown in the illustrated embodiment. The patient continues to bite on the airway device 10, keeping it in the working position maintaining the thrusted jaw position and unobstructed airway condition.

Figure 5:
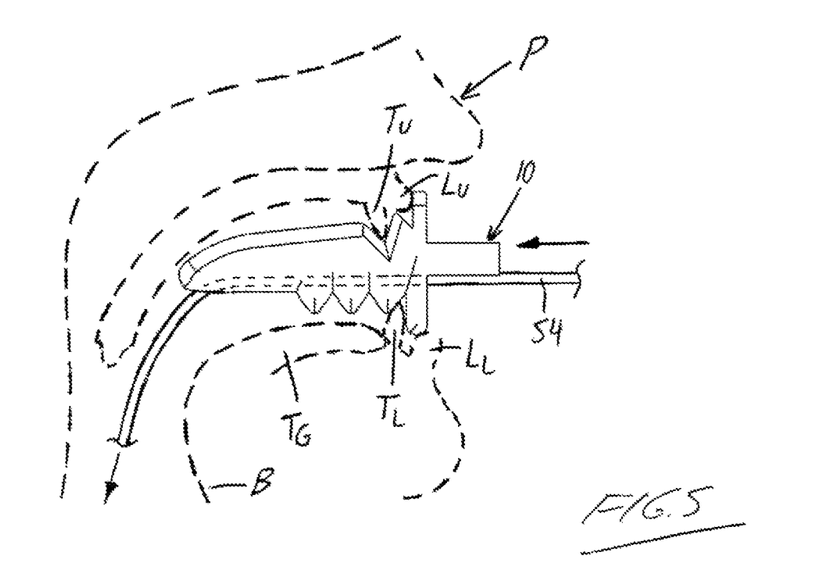
FIG. 5 illustrates use of a longitudinal open-sided channel in the airway device to feed a bronchoscope into the trachea of a patient.
Figure 6:
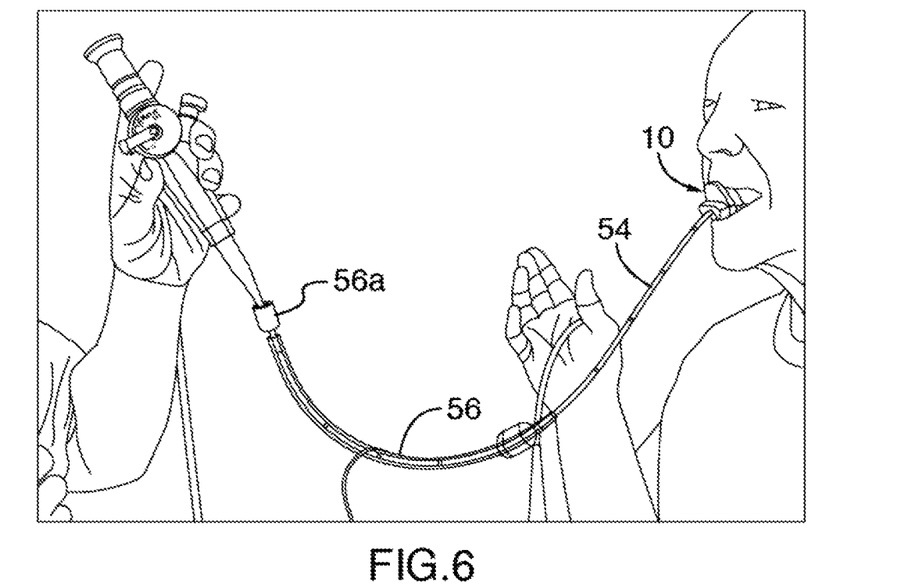
FIG. 6 illustrates an endotracheal tube on a bronchoscope that has been fed into place through the channel of the airway device in accordance with FIG. 5.

Next, referring to FIG. 5, with an endotracheal tube loaded on a bronchoscope 54, the distal end of the bronchoscope 54 is inserted into the inlet opening of the longitudinal channel 50 at the proximal end 14 of the airway device 10, and fed along the underside of the airway device through the longitudinal channel 50 to the downturned wall 52 at the far end thereof, where the concave curvature of the downturned wall 52 helps direct the distal end of the bronchoscope 54 downwardly from the underside of the airway device 10 and well into the patient's trachea. FIG. 5 illustrates feeding of the bronchoscope into place, and FIG. 6 shows the bronchoscope together with the endotracheal tube 56 that is slidably fitted thereon.

Figure 7:
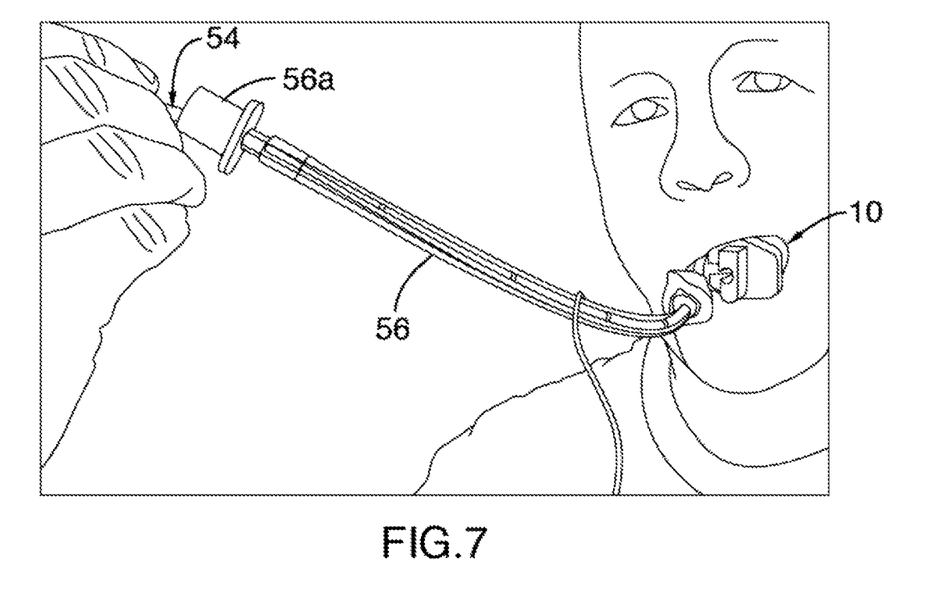
FIG. 7 illustrates rolling of the airway device from off the bronchoscope of FIG. 6 into a lateral position between anterior teeth on one side of the patient's dental arch in order to enable feeding of the endotracheal tube along the bronchoscope, past the laterally offset airway device into the patient's trachea.

With the bronchoscope now fed into place through the channel 50 in the underside of the airway device 10, the airway device now rests in a position embracing downwardly over the bronchoscope 54 on both sides. The patient opens their mouth to release the airway device from its working position clamped between the anterior and maxillary and mandibular teeth, at which point the practitioner grips the airway device by the grip tab 26 at the proximal end 14 outside the patient's mouth. With the airway device 10 freed from the patient's bite, the practitioner rotates the airway device 10 about a longitudinal axis thereof, thereby withdrawing the airway device 10 from the position embracing about the bronchoscope 54 by relative movement of the bronchoscope out of the open bottom of the longitudinal channel 50 in the underside of the device 10. As part of, or after, this rotational separation of the airway device from the bronchoscope, the practitioner moves the airway device 10 laterally outward into a position between these posterior mandibular and maxillary teeth (premolar and molars) at one side of the patient's dental arch, and lodges the airway device between these posterior teeth, as shown in FIG. 7. Here, the airway device will act as a bite block to protect the bronchoscope from any chance of damage from biting.

Shifted laterally to one side of the mouth, the airway device 10 leaves room at the medial center and other side of the mouth to accommodate sliding of the endotracheal tube 56 along the bronchoscope and past the offset airway device into the trachea. At this point, the bronchoscope 54 can be withdrawn back out of the patient via this same accommodating space beside the airway device. Unlike prior art airway devices in which the endotracheal tube 56 is passed through the airway device via a through-bore that is closed on all sides, removal of the airway device 10 from the patient's mouth after successful placement of the endotracheal tube 56 requires no removal of the endotracheal tube connector 56a, as the airway device 10 was already separated from the bronchoscope 54 by the aforementioned rolling action before insertion of the endotracheal tube 56 along the bronchoscope 54.

While the illustrated embodiment places the longitudinal channel 50 in the underside of the airway device 10 so as to have an open-bottom channel that's rolled off of the bronchoscope 54 from a position embracing thereover, other embodiments may alternatively place an open-top longitudinal channel in the topside of the airway device, in which case the airway device 10 embraces the bronchoscope 54 from thereunder until the device 10 is rolled out from beneath the bronchoscope 54 through an open top side of the topside channel.

Since the airway device is separated from the bronchoscope prior to feeding the endotracheal tube into place, the cross-sectional area of the longitudinal channel may be intentionally undersized with a width smaller than the outer diameter of endotracheal tube since the tube is not passed through the channel, thereby further distinguishing the open-sided longitudinal channel from the fully enclosed through-bores of the prior art airways that accommodate passage of the endotracheal tube therethrough.

In one embodiment, the airway device is a disposable device pre-packaged in sterile condition in a blister pack or the like for quick dispensing, particularly for use in ventilation applications requiring quick deployment. However, other re-usable embodiments requiring sterilization between uses are also contemplated herein.

While the illustrated embodiment involves particular use of the airway device with a bronchoscope during placement of an endotracheal tube in the patient's trachea, it will be appreciated that the airway device may also be used in other procedures relying on oral introduction of an endoscope to a target destination in the patient's body, whether that endoscope is a bronchoscope, gastroscope, or other type of endoscope.

While exemplary aspects and embodiments have been described above, those of skill in the art will recognize that various modifications can be made, and many apparently widely different embodiments of same made within the scope of the claims without departure from such scope. As such, it is intended that all matter contained within the specification shall be interpreted as illustrative only and not in a limiting sense.

All publications, patents and patent applications are herein incorporated by reference in their entirety to the same extent as if each individual publication, patent or patent application was specifically and individually indicated to be incorporated by reference in its entirety.

The invention claimed is:

1. An airway device comprising a unitary body having a topside and an opposing underside separated in a height direction of said unitary body, a proximal end and opposing distal end separated in a longitudinal direction of said body, a transversely oriented upper notch defined in the topside of the unitary body for receipt of anterior maxillary teeth of a patient within said upper notch in a working position of the airway device, and one or more transversely oriented lower notches defined in the underside of the unitary body for receipt of anterior mandibular teeth of the patient within one of said one or more lower notches in the working position of the airway device, said one of said one or more lower notches being positioned relative to the upper notch in a longitudinal direction of the airway device so as to position the patient's mandible in a protracted position to encourage an unobstructed state of the patient's airway in the working position of the airway device, said unitary body further comprising a longitudinal channel recessed into either the underside or the topside of the unitary body and spanning longitudinally from the proximal end of the unitary body to an outlet end of the longitudinal channel that is adjacent to the opposing distal end of the unitary body, said channel being characterized by an open top or open bottom thereof that spans a full longitudinal length of said longitudinal channel at the topside or underside of the unitary body, and wherein among said upper notch and said one or more lower notches, there is at least one split-notch composed of two half-notches residing on opposing sides of the open top or open bottom of the longitudinal channel.

2. A method of using the airway device of claim 1 in combination with an endoscope, said method comprising, with the airway device in the working position received between the anterior maxillary and mandibular teeth of the patient that are respectively engaged in the upper notch and the one of the one or more lower notches at the topside and the underside of the unitary body of said airway device, and with the mandible of the patient in the protracted position maintained by engagement of said anterior maxillary and mandibular teeth in said upper and lower notches, and with an endoscope in a position reaching through the longitudinal channel of the airway device to a target destination in the patient, withdrawing the longitudinal channel of the airway device from an embraced position about the endoscope by freeing the endoscope from the longitudinal channel through the open top or bottom thereof at the topside or underside of the unitary body of the airway device.

3. The airway device of claim 1 wherein the longitudinal channel, at the outlet end thereof, is terminated in the longitudinal direction by a curved and downturned wall, which is positioned to guide an endoscope downwardly toward a target destination when fed through said longitudinal channel.

4. The airway device of claim 3 wherein said longitudinal channel is recessed in the underside of the unitary body and is characterized by said open bottom spanning the full longitudinal length of said longitudinal channel at the underside of the unitary body, and said at least one split-notch is embodied by said one or more lower notches.

5. The airway device of claim 4 wherein said one or more lower notches comprises a plurality of lower notches, said at least one split-notch is a plurality of split-notches, and each one of said lower notches is one of said split-notches.

6. The airway device of claim 1 wherein said longitudinal channel is recessed in the underside of the unitary body and is characterized by said open bottom spanning the full longitudinal length of said longitudinal channel at the underside of the unitary body, and said at least one split-notch is embodied by said one or more lower notches.

7. The airway device of claim 6 wherein said one or more lower notches comprises a plurality of lower notches, said at least split-notch is a plurality of split-notches, and each one of said lower notches is one of said split-notches.

8. A method of preparing a patient for ventilation by a bag-mask resuscitator, the method comprising:
   placing the airway device of claim 1 in the working position in which the anterior maxillary teeth of the patient engage said upper notch in the topside of the unitary body of the airway device and the anterior mandibular teeth of the patient engage in said one of the one or more lower notches in the underside of the unitary body of the airway device, thereby achieving the protracted position of the patient's mandible and encouraging the unobstructed state in the patient's airway; and
   simultaneously and one handedly urging hinged closure of the mandible toward the maxilla to maintain the working position of the airway device between maxillary and mandibular teeth while urging a mask of a bag-mask resuscitator against a facial area of the patient.

9. A method comprising:
   (a) with the airway device of claim 1 received between the anterior maxillary and mandibular teeth of the patient with the mandible of the patient in the protracted position maintained by engagement of the anterior maxillary teeth in the upper notch and the anterior mandibular teeth in the one of the one or more lower notches, passing a distal end of an endoscope through the longitudinal channel to a target destination in the patient; and
   (b) while maintaining the distal end of the endoscope at the target destination, withdrawing the longitudinal channel of the airway device from an embraced position about the endoscope by freeing the endoscope from the longitudinal channel through the open top or open bottom thereof at the topside or underside of the unitary body of the airway device.

10. The method of claim 9 wherein the longitudinal channel, at the outlet end thereof, is terminated in the longitudinal direction by in a curved and downturned wall, and step (a) comprises using said curved and downturned wall to guide the endoscope downwardly toward the target destination.

11. The method of claim 9 wherein the longitudinal channel is recessed in the underside of the unitary body of the airway device, and the open top or bottom through which the endoscope is freed in step (b) is an open bottom of said longitudinal channel.

12. The method of claim 9 wherein the endoscope is a bronchoscope, the target destination is the patient's trachea, and freeing of the bronchoscope from the airway device enables feeding of an endotracheal tube along said bronchoscope into the patient's trachea independently of the airway device.

13. The method of claim 12 further comprising, with the airway device still present in the patient's mouth and still separated from the bronchoscope, feeding the endotracheal tube along the bronchoscope past the airway device and into the patient's trachea.

14. The method of claim 9 wherein the endoscope is a gastroscope.

15. A method comprising:
   (a) providing an airway device having a body having a topside and an opposing underside separated in a height direction of said body, a proximal end and opposing distal end separated in a longitudinal direction of said body, an upper notch defined in the topside of the body and extending in a lateral direction transverse to the longitudinal and height directions for receipt of anterior maxillary teeth of a patient in said upper notch, a lower notch defined in the underside of the body and extending in the lateral direction for receipt of anterior mandibular teeth of the patient in said lower notch, and a longitudinal channel recessed into either the underside or the topside of the body and spanning longitudinally from the proximal end of the body toward the opposing distal end thereof;
   (b) with the airway device received between the anterior maxillary and mandibular teeth of the patient with the mandible of the patient in a protracted position maintained by engagement of the anterior maxillary and mandibular teeth in the upper and lower notches respectively, passing a distal end of an endoscope through the longitudinal channel to a target destination in the patient; and
   (c) while maintaining the distal end of the endoscope at the target destination, withdrawing the longitudinal channel of the airway device from an embraced position about the endoscope by freeing the endoscope from the longitudinal channel through an open top or bottom thereof at the topside or underside of the airway device;
   wherein withdrawing the longitudinal channel of the airway device from the embraced position comprises moving the airway device into a lateral position received between posterior maxillary and mandibular teeth on one side of the patient's dental arch, where the airway device serves as a bite block to protect the endoscope from biting.

16. A method comprising:
   (a) providing an airway device having a body having a topside and an opposing underside separated in a height direction of said body, a proximal end and opposing distal end separated in a longitudinal direction of said body, an upper notch defined in the topside of the body and extending in a lateral direction transverse to the longitudinal and height directions for receipt of anterior maxillary teeth of a patient in said upper notch, a lower notch defined in the underside of the body and extending in the lateral direction for receipt of anterior mandibular teeth of the patient in said lower notch, and a longitudinal channel recessed into either the underside or the topside of the body and spanning longitudinally from the proximal end of the body toward the opposing distal end thereof;

(b) with the airway device received between the anterior maxillary and mandibular teeth of the patient with the mandible of the patient in a protracted position maintained by engagement of the anterior maxillary and mandibular teeth in the upper and lower notches respectively, passing a distal end of an endoscope through the longitudinal channel to a target destination in the patient; and (c) while maintaining the distal end of the endoscope at the target destination, withdrawing the longitudinal channel of the airway device from an embraced position about the endoscope by freeing the endoscope from the longitudinal channel through an open top or bottom thereof at the topside or underside of the airway device;

wherein withdrawing the longitudinal channel of the airway device from the embraced position comprises using a rolling motion of the airway device about a longitudinal axis to withdraw the longitudinal channel from about the endoscope.

\* \* \* \* \*